(12) United States Patent
Klemm et al.

(10) Patent No.: US 8,499,085 B2
(45) Date of Patent: Jul. 30, 2013

(54) ADVANCED AVAILABILITY DETECTION

(75) Inventors: Reinhard Peter Klemm, Basking Ridge, NJ (US); Lynne Shapiro Brotman, Westfield, NJ (US)

(73) Assignee: Avaya, Inc., Basking Ridge, NJ (US)

( * ) Notice: Subject to any disclaimer, the term of this patent is extended or adjusted under 35 U.S.C. 154(b) by 815 days.

(21) Appl. No.: 12/645,866

(22) Filed: Dec. 23, 2009

(65) Prior Publication Data

US 2010/0235524 A1  Sep. 16, 2010

Related U.S. Application Data

(60) Provisional application No. 61/160,572, filed on Mar. 16, 2009.

(51) Int. Cl.
*G06F 15/16* (2006.01)
*G06F 12/00* (2006.01)

(52) U.S. Cl.
USPC .......................................... 709/228; 709/250

(58) Field of Classification Search
USPC .................. 709/217–218, 223–229, 250
See application file for complete search history.

(56) References Cited

U.S. PATENT DOCUMENTS

| | | | |
|---|---|---|---|
| 7,424,537 B2 | 9/2008 | Bennett et al. | |
| 7,529,683 B2 | 5/2009 | Horvitz et al. | |
| 7,603,464 B2 | 10/2009 | White | |
| 7,689,657 B2 | 3/2010 | Daniell et al. | |
| 7,693,509 B2 | 4/2010 | Miyata | |
| 7,958,453 B1 | 6/2011 | Taing | |
| 7,970,384 B1 | 6/2011 | Lambert et al. | |
| 8,082,302 B2 | 12/2011 | Becker et al. | |
| 8,190,705 B2 | 5/2012 | Bennett et al. | |
| 8,358,762 B1 | 1/2013 | Renner et al. | |
| 2004/0143603 A1 | 7/2004 | Kaufmann et al. | |
| 2006/0004911 A1 | 1/2006 | Becker et al. | |
| 2006/0015609 A1 | 1/2006 | Hagale et al. | |
| 2006/0072721 A1 | 4/2006 | Wisniewski | |
| 2006/0253593 A1 | 11/2006 | Jachner | |
| 2007/0004385 A1 | 1/2007 | Horvitz et al. | |
| 2007/0130260 A1 | 6/2007 | Weintraub et al. | |
| 2007/0186007 A1 | 8/2007 | Field et al. | |
| 2008/0133742 A1 | 6/2008 | Southiere et al. | |
| 2008/0240384 A1 | 10/2008 | Suryanarayana et al. | |
| 2008/0261630 A1 | 10/2008 | Wormald et al. | |
| 2008/0281783 A1 | 11/2008 | Papkoff et al. | |

(Continued)

FOREIGN PATENT DOCUMENTS

| | | |
|---|---|---|
| CN | 1901513 A | 1/2007 |
| EP | 1505529 A1 | 2/2005 |

(Continued)

OTHER PUBLICATIONS

Noll, Joachim, "PCT Application No. PCT/US2010/027396 Jun. 11, 2010", , Publisher: PCT, Published in: PCT.

(Continued)

*Primary Examiner* — Zarni Maung

(57) ABSTRACT

A method is provided in which the present invention is for a method in which a telecommunications terminal determines whether its user is available to accept an incoming invitation to participate in a telecommunications session based on: (1) a characteristic of the use of a software application, (2) a characteristic of the use of a resource of a terminal, (3) a sensor input, (4) a characteristic of the incoming invitation or (5) any combination of (1), (2), (3), (4), and (5).

14 Claims, 13 Drawing Sheets

U.S. PATENT DOCUMENTS

| | | |
|---|---|---|
| 2009/0216725 A1 | 8/2009 | Yaqub |
| 2010/0306327 A1 | 12/2010 | Shinkawa et al. |
| 2013/0041953 A1 | 2/2013 | Renner et al. |

FOREIGN PATENT DOCUMENTS

| | | |
|---|---|---|
| FR | 2814022 | 3/2002 |
| JP | 2003-271204 | 9/2003 |
| JP | 2005-045724 | 2/2005 |
| JP | 2005-110026 | 4/2005 |
| JP | 2005-110028 | 4/2005 |
| JP | 2005-268954 | 9/2005 |
| JP | 2006-119415 | 8/2006 |
| JP | 2006-229415 | 8/2006 |
| JP | 2006-333040 | 12/2006 |
| JP | 2008-118409 | 5/2008 |
| JP | 2008-160753 | 7/2008 |
| JP | 2008-182465 | 8/2008 |
| WO | 0169432 A2 | 9/2001 |

OTHER PUBLICATIONS

Wheeler, Owen, "GB Application No. GB1004182.0 Office Action Jul. 16, 2010", , Publisher: UK IPO, Published in: GB.

Wheeler, Owen, "GB Application No. GB1004183.8 Office Action Jul. 16, 2010", , Publisher: UK IPO, Published in: GB.

ADVANCED AVAILABILITY DETECTION

CROSS-REFERENCE TO RELATED APPLICATIONS

This application claims the benefit of U.S. provisional application Ser. No. 61/160,572, filed Mar. 16, 2009, entitled Presence Based on the Context or Persona of the Party Being Contacted, which is also incorporated by reference.

FIELD OF THE INVENTION

The present invention relates to telecommunications in general, and, more particularly, to availability detection.

BACKGROUND OF THE INVENTION

The term "availability" in the context of telecommunications refers to whether a user is available to accept incoming invitations to participate in telecommunications sessions. For example, a user may be unavailable to accept telephone calls if the telephone line is busy. In instant messaging, a user is unavailable if the user's online status is set to "busy." In the latter case, online status is set manually through a "Change Online Status" menu which is commonly available in instant messaging clients.

Telecommunications devices use availability information to decide whether to accept incoming telecommunications, alert users of incoming telecommunications, display incoming telecommunications, and other purposes. Availability detection, as implemented in existing applications, reflects either the utilization of telecommunications channels or the express unwillingness of users to participate in telecommunications.

At present, availability detection suffers from at least two drawbacks. First, the "availability" of a user reflects only the user's preferences; it does not account for situations in which a user's availability needs to reflect the preferences of third parties. For instance, in the employment setting, it is desirable for both employees, as well as employers to have a say whether the employees are available. Second, users often forget to manually reset their online status, and consequently, it is difficult to know when one's online status is a true reflection of his or her availability.

Therefore, the need exists for a method which addresses these drawbacks to provide improved and more robust telecommunications devices.

SUMMARY OF THE INVENTION

The present invention addresses the drawbacks of the prior art by providing a method that determines user availability on the basis of both the virtual and physical environments of a user.

More specifically, the present invention is for a method in which a telecommunications terminal determines whether its user is available to accept an incoming invitation to participate in a telecommunications session based on:
  (1) a characteristic of the use of a software application component, or
  (2) a characteristic of the use of a resource of a terminal, or
  (3) a sensor input, or
  (4) a characteristic of the incoming invitation, or
  (5) any combination of (1), (2), (3) and (4).
When an invitation to participate in a telecommunications session is received at a telecommunications terminal, the present invention determines user availability. Based on the availability determination, the present invention accepts the incoming invitation or rejects it.

Additionally, the present invention, in some of its embodiments, provides a method for the centralized enforcement of availability policies. For the purposes of this specification, the term "availability policy" is defined as a set of one or more rules which determine when a user is available for telecommunications.

In a first embodiment of the present invention, user availability is determined according to a characteristic of the use of a software application component. For the purposes of this specification, the term "characteristic of the use of a software application component" is defined as any item of information concerning the manner in which a specific software application component is used. For example, and without limitation, such characteristics include: addresses that were visited by a web browser, a keyword located in an instant message, a keyword in a document open for editing, identity of specific software application components used, and others.

For the purposes of this specification "a software application component" is a part of a software application which provides functionality for users of the software application. Software application components are defined by underlying application executable code. Different software application components may share executable code. However, the executable code for one component is not completely identical to the executable code for another component if the two components are to provide different functionalities. Stated succinctly, two different software application components must differ in at least one line of code (either machine executable code or higher-level programming language code).

In one instance of its first embodiment, the present invention determines availability based on one or more web sites that have been visited by a web browser. In accordance with this embodiment of the present invention, the websites serve as a clue whether the user of the web browser is available to accept invitations for telecommunications sessions. For example, if the user visits entertainment web sites such as Movies.com™, this is an indication that the user is using his or her telecommunications terminal for personal entertainment and not in relation to the user's employment. In accordance with an availability policy of this example, when a user is found to be visiting Movies.com™, the user is considered available to participate in telecommunications.

In another instance of its first embodiment, the present invention identifies one or more keywords which are typed in documents that are open for editing on the user's computer. In accordance with this embodiment, the keywords serve as a basis for determining whether the user is available to take part in telecommunications. For example, and without limitation, if an open document contains Internet slang words, this is an indication that the user is engaged in a personal conversation and not in employment-related matters. Accordingly, the user is considered available to participate in telecommunications when Internet slang words are identified in a document.

In a third instance of its first embodiment, the present invention identifies specific application components that are, or have been, used. This information serves as a basis for determining whether a user is available to take part in telecommunications. For example, and without limitation, a web browser may comprise a web-conferencing component and an animation component. The web-conferencing component is a plug-in which allows the user to participate in company web conferences. Such conferences are strictly business-related. The animation component allows the user to view videos on Youtube.com™. When the animation component is used, the user of the terminal, on which the browser is running, is most likely engaged in the viewing of Youtube.com™ videos for personal entertainment. In accordance with an availability policy of this example, the user is considered unavailable to participate in telecommunications when the web conferencing component is used.

In general, the policies of the above examples consider a user available when the user is not engaged in an employment-related activity. Although, the rationale behind the policies is increasing employee productivity, the scope of the present invention is not limited to any particular set of policies. The policies which the present invention implements are determined by the needs of the users of the invention.

In accordance with a second embodiment of the present invention, a measurement of the use of a resource of a terminal is obtained. For the purposes of this specification, the term "characteristic of the use of a resource of a terminal" is defined as any information concerning at least one of: (1) whether a particular hardware component or peripheral device of the terminal is used at all; and (2) the load and/or utilization rate of a hardware component or peripheral device.

In one instance of its second embodiment, the present invention determines availability on the basis of a keystroke rate. In accordance with the availability policy of this embodiment, all incoming invitations to the user to participate in a telecommunications session are declined when the user's keystroke rate exceeds a particular threshold of keystrokes per unit time. The rationale for this policy is that if a user is typing fast, the user is most likely devoting his full attention to preparing a document and he or she is unwilling to be disturbed by incoming telecommunications.

In another instance of its second embodiment, the present invention determines availability on the basis of a cache miss rate. In accordance with the availability policy of this embodiment, all incoming invitations to the user to participate in a telecommunications session are declined when the cache miss pattern is similar to a cache miss pattern that is specified in an availability policy. The cache miss rate provides information about the type of activity in which the user of a telecommunications terminal is engaged. For example, when a user generates many cache misses, the user is likely engaged in manipulating a large data set, such as a large spreadsheet. In this example, when there are indications that a user is involved in work with spreadsheets, the user is unavailable for incoming telecommunications. Just like the exemplary policies described with respect to the first embodiment, the rule of this example promotes increased employee productivity by ensuring that telecommunications terminal users are not disturbed when their use of resources indicates that they are engaged in a productive activity.

In a third illustrative embodiment of the present invention, user availability is determined on the basis of information about the user's physical surroundings. In accordance with the third embodiment, user availability is determined on the basis of input from sensors. The sensors comprise physiological sensors, motion sensors, and others.

In one instance of its third embodiment, the present invention uses signal from a motion sensor that is placed in the chair of a user. The motion sensor detects how much the user shifts in his or her seat. In accordance with the availability policy of this embodiment, all incoming invitations to participate in a telecommunications session are declined when the motion sensor provides a feedback that exceeds a threshold of movements per unit time. The rationale for such an arrangement is that if a user does not move in his or her seat, this is an indication that the user has devoted his full attention to performing a task and he is likely unwilling to accept telecommunications.

In another instance of its third embodiment, the present invention determines availability on the basis of input from a temperature sensor. In accordance with the availability policy of this embodiment, all incoming invitations to the user to participate in a telecommunications session are declined when the temperature falls below a certain threshold. The rationale for such an arrangement is that if it is too cold in a room, it is likely that no one is present in it.

In a fourth embodiment of the present invention, availability is determined on the basis of a characteristic of the incoming invitation to participate in a telecommunications session. For the purposes of this disclosure, the term "characteristic of an invitation to participate in a telecommunications session" is defined as at least one of (1) information about the user initiating the telecommunications session, (2) topic of the telecommunications session, (3) expected duration of the telecommunications session, and (4) priority rating for the telecommunications session.

It is to be understood, that the above embodiments and their instances are provided to better illustrate different aspects of the present invention. They are in no way exhaustive of the full scope of the invention. The following disclosure teaches examples of some embodiments of the present invention in detail.

DETAILED DESCRIPTION

Figure 1:
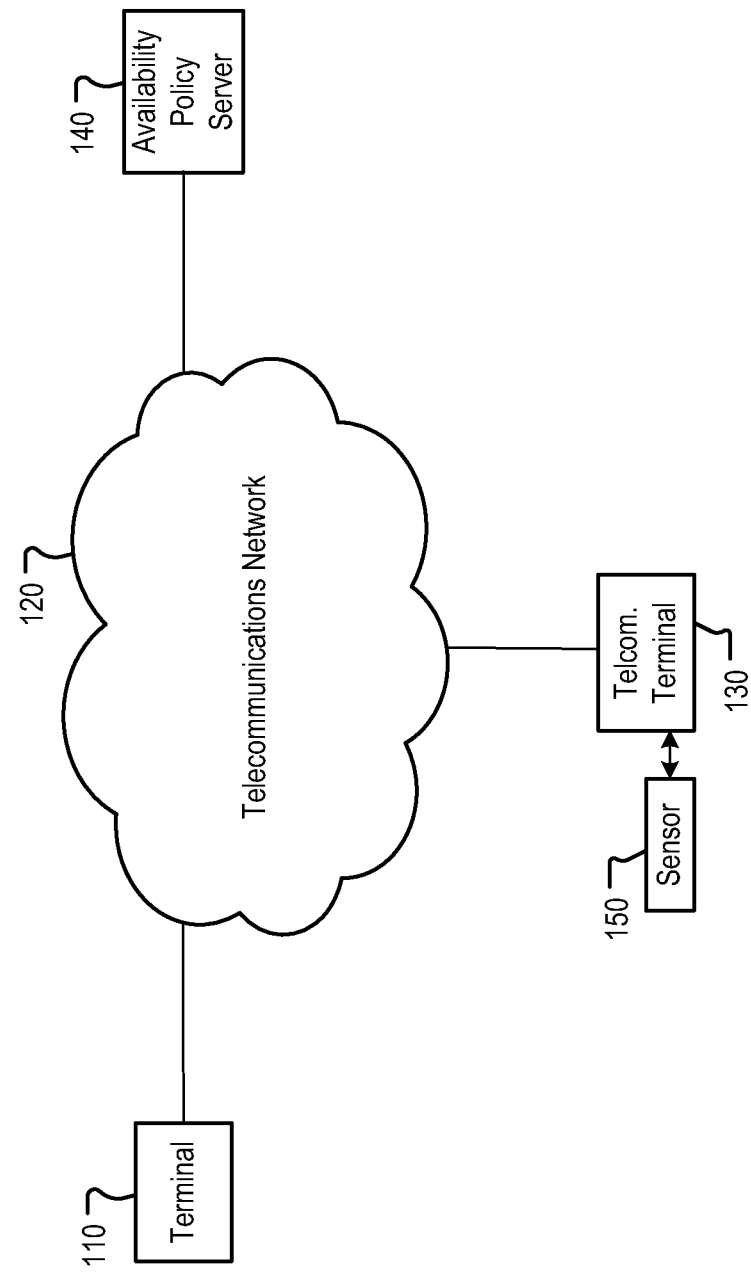
FIG. 1 depicts a schematic diagram of the salient components of the illustrative embodiment of the present invention.

FIG. 1 depicts a schematic diagram of the salient components of the illustrative embodiment of the present invention. The illustrative embodiment comprises terminal 110, telecommunications network 120, policy server 140, sensor 150, and terminal 130.

Terminal 110 is a desk set telephone receiver. In accordance with the illustrative embodiment of the present invention, terminal 110 is capable of both voice and video telecommunications, but it will be clear to those skilled in the art, after reading this disclosure, how to make and use alternative embodiments of the present invention in which terminal 110 has only a voice capability. Furthermore, it will be clear to those skilled in the art, after reading this disclosure, how to make and use alternative embodiments of the present invention in which terminal 110 is another telecommunications device (e.g. soft phone, cellular telephone, 2-way radio, portable digital assistant, etc.).

Telecommunications network 120 transports signals between terminal 110, terminal 130, and policy server 140. In accordance with the illustrative embodiment of the present invention, telecommunications network 120 is the Internet, but it will be clear to those skilled in the art, after reading this disclosure, how to make and use alternative embodiments of the present invention in which telecommunications network 120 is any type of telecommunications network (e.g. local area network, the Public Switched Telephone Network, SONET, ATM, cellular network, etc.).

Terminal 130 is a telecommunications terminal. In accordance with the illustrative embodiment of the present invention, terminal 130 is capable of conducting both audio and video telephone calls, but it will be clear to those skilled in the art, after reading this disclosure, how to make and use alternative embodiments of the present invention in which terminal 130 has only a voice capability. Furthermore, it will be clear to those skilled in the art, after reading this disclosure, how to make and use alternative embodiments of the present invention in which terminal 130 is any type of telecommunications device (e.g. cellular telephone, 2-way radio, portable digital assistant, desk set telephone receiver, etc.).

Policy server 140 is a server which stores availability policy rules. In accordance with the illustrative embodiment of the present invention, terminal 130 receives availability policy rules from policy server 140. However, it will be clear to those skilled in the art, after reading this disclosure, how to make and use alternative embodiments of the present invention in which terminal 130 obtains the availability policy rules from another source (e.g. the rules are loaded manually on the terminal by an administrator or by the user of terminal 130, etc.). Furthermore, in accordance with the illustrative embodiment of the present invention, the availability policy rules stored at policy server 140 are specified by the user of terminal 130, but it will be clear to those skilled in the art, after reading this disclosure, how to make and use alternative embodiments of the present invention in which the availability policy rules are specified by a network administrator, or by the designers of availability detector 237.

Sensor 150 is a plurality of sensors that are capable of supplying data to terminal 130. Although, in accordance with the illustrative embodiment of the present invention, sensor 150 is a collection of three sensors, it will be clear to those skilled in the art, after reading this disclosure, how to make and use alternative embodiments of the present invention in which sensor 150 includes any number of sensors (e.g. 1, 2, 5, 10, 15, etc.) Sensor 150 is further described in the discussion with respect to FIG. 2.

Figure 2:
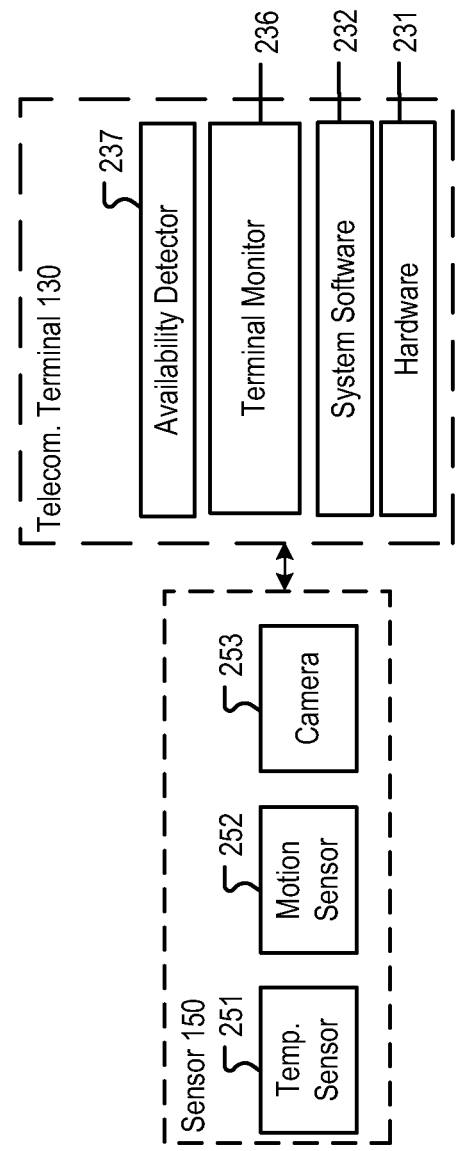
FIG. 2 depicts a schematic diagram of the salient components of the illustrative embodiment of the present invention.

FIG. 2 depicts a schematic diagram of the salient components of the illustrative embodiment of the present invention. The illustrative embodiment comprises sensor 150, terminal 130, temperature sensor 251, motion sensor 252, camera 253, hardware 231, system software 232, terminal monitor 236, and availability detector 237.

Telecommunications terminal 130 comprises hardware 231, system software 232, terminal monitor 236, and availability detector 237.

Hardware 231 is the electronic components that comprise terminal 130, such as, for example, and without limitation, processor (single-core or multi-core), memory, transceiver, network interface, display, sound interface, video interface, etc. Hardware 231 is capable of executing system software and one or more applications. In accordance with the illustrative embodiment of the present invention, hardware 231 is executing terminal monitor 236 and system software 232. It will be clear to those skilled in the art how to make and use hardware 231.

System software 232 is an operating system instance that is executing on hardware 231.

Terminal monitor 236 is software for obtaining information about terminal 130. In accordance with the illustrative embodiment of the present invention, terminal monitor 236 performs at least one of two functions:
  i. Obtaining one or more characteristics of the use of a software application component that is running on terminal 130.
  ii. Obtaining a measurement of the use of one or more resources of terminal 130.

Figure 3:
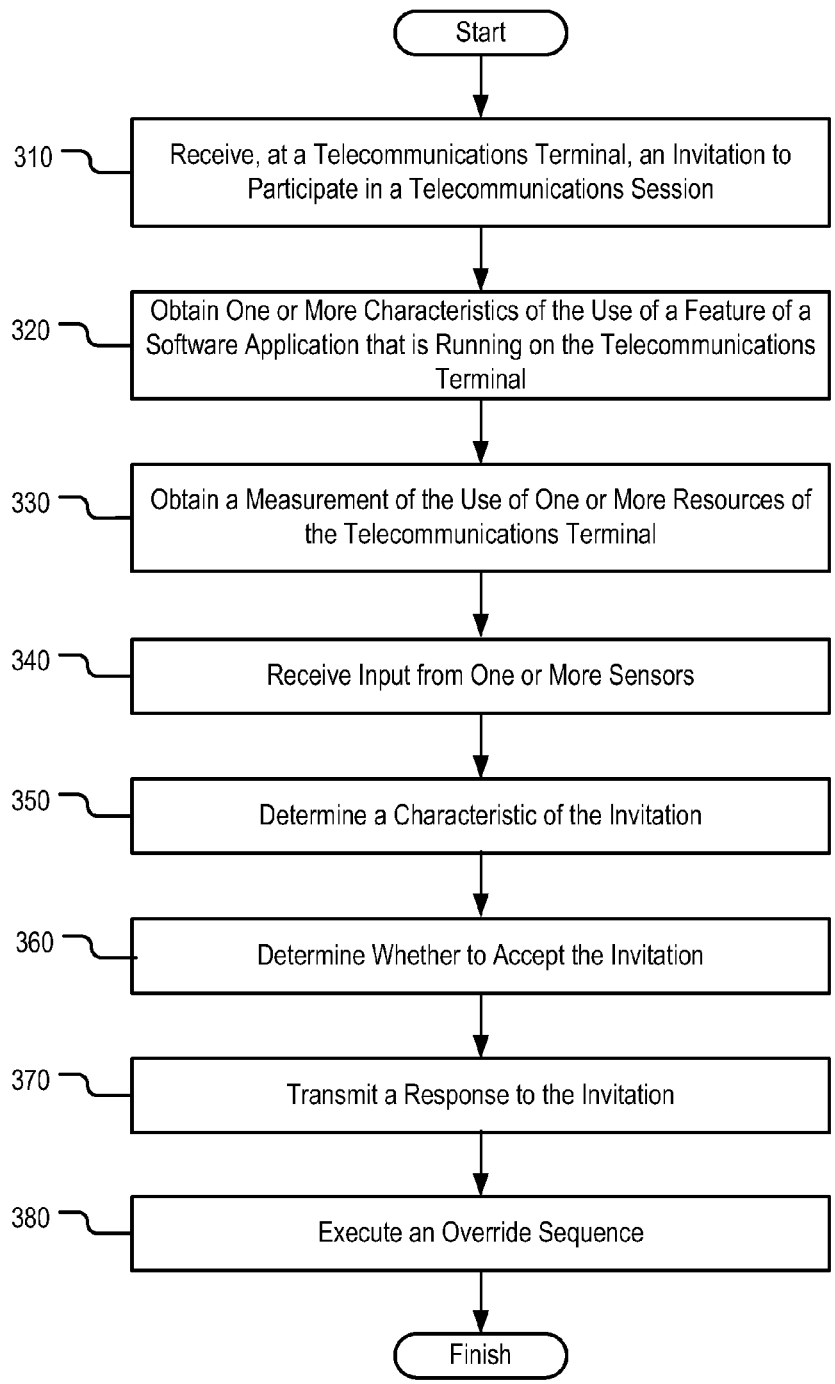
FIG. 3 depicts a flowchart of the execution of the salient tasks associated with the operation of the illustrative embodiment of the present invention.

The operation of terminal monitor 236 is described in further detail in the discussion with respect to FIG. 3.

Availability detector 237 is software for determining whether the user of terminal 130 is available to participate in a telecommunications session. The operation of availability detector 237 is further described in the discussion of FIGS. 7-13.

Sensor 150 comprises temperature sensor 251, motion sensor 252, and camera 253.

Temperature sensor 251 is a temperature sensor.

Motion sensor 252 is a motion sensor. In accordance with the illustrative embodiment of the present invention, sensor 252 is an electronic motion detector that uses infra red (IR) technology. However, it will be clear to those skilled in the art, after reading this disclosure, how to make and use alternative embodiments of the present invention in which other sensors are used (e.g. ultrasonic, microwave, hall effect, etc.).

Camera 253 is a video camera. However, it will be clear to those skilled in the art, after reading this disclosure, how to make and use alternative embodiments of the present invention in which camera 253 is a still image camera.

FIG. 3 depicts a flowchart of the execution of the salient tasks associated with the operation of the illustrative embodiment of the present invention. It will be clear to those skilled in the art, after reading this disclosure, how to perform the tasks associated with FIG. 3 in a different order than represented or to perform one or more of the tasks concurrently. Furthermore, it will be clear to those skilled in the art, after reading this disclosure, how to make and use alternative embodiments of the present invention that omit one or more of the tasks.

At task 310, terminal 130 receives an invitation to participate in a telecommunications session. The invitation is transmitted from terminal 110. In accordance with the illustrative embodiment of the present invention, the telecommunications session is a telephone call. However, it will be clear to those skilled in the art, after reading this disclosure, how to make and use alternative embodiments of the present invention in which the telecommunications session is any other type of telecommunications session, such as, for example, and without limitation, a video call, a chat conversation, teleconference, and others.

At task 320, availability detector 237 obtains a characteristic of the use of a software application component. The characteristic is obtained from terminal monitor 236. For example, and without limitation, a software application, such as Outlook™, can provide multiple components such as an email client, calendar, and tasks scheduler. The illustrative embodiment of the present invention monitors aspects of the use of such individual components. Task 320 is further described in the discussion with respect to FIG. 4.

At task 330, availability detector 237 obtains a measurement of the use of one or more resources of terminal 130. The measurement is obtained from terminal monitor 236. Task 330 is further described in the discussion with respect to FIG. 5.

At task 340, terminal 130 receives input from sensor 150. Task 340 is further described in the discussion with respect to FIG. 6.

At task 350, terminal 130 determines a characteristic of the invitation to participate in a telecommunications session. Task 350 is further described in the discussion with respect to FIG. 7.

At task 360, terminal 130 determines whether to accept the invitation received at task 310. Task 360 is further described in the discussion with respect to FIG. 8.

At task 370, terminal 130 in a well known fashion transmits a response to the invitation to participate in a telecommunications session. In accordance with the illustrative embodiment of the present invention, the response is either an acceptance or a rejection. However, it will be clear to those skilled in the art, after reading this disclosure, how to make and use alternative embodiments of the present invention in which a message is transmitted to terminal 110 which identifies an action to be taken by the far-end party, such as, for example, and without limitation, call back later, use another medium of communication, and others. Furthermore, it will be clear to those skilled in the art, after reading this disclosure, how to make and use alternative embodiments of the present invention in which the message contains an indication of additional information concerning the telecommunications session, such as, for example, and without limitation, a preferred communication medium (e.g. voice, text, etc.), preferred alternative time to conduct a telecommunications session, and others.

And still furthermore, it will be clear to those skilled in the art, after reading this disclosure, how to make and use alternative embodiments of the present invention in which terminal 130 accepts the call and puts the far-end party on hold. The time for which the far-end party is put on hold can be determined according to an availability policy rule. In further embodiments, the present invention transmits a message to the far-end party indicating that he or she is being put on hold.

At task 380, terminal 130 executes an override sequence. The override sequence is executed when terminal 130 declines the invitation to participate in a telecommunications session. When this is the case, the user of terminal 110 is given the option to enter a password in order to override the decision of terminal 130 and force it to accept the incoming invitation. Task 380 is further described in the discussion with respect to FIG. 13.

Figure 4:
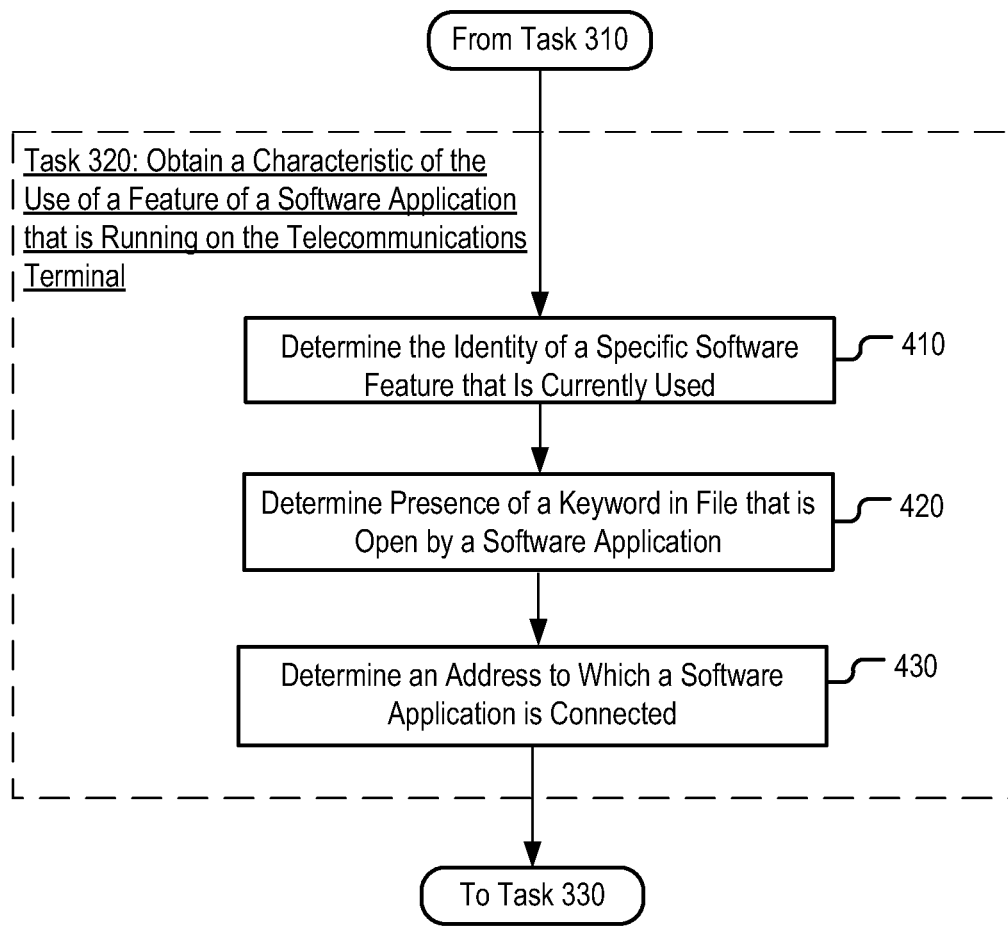
FIG. 4 depicts a flowchart of the execution of the salient subtasks associated with the performance of task 320.

FIG. 4 depicts a flowchart of the execution of the salient subtasks associated with the performance of task 320. It will be clear to those skilled in the art, after reading this disclosure, how to perform the tasks associated with FIG. 4 in a different order than represented or to perform one or more of the tasks concurrently. Furthermore, it will be clear to those skilled in the art, after reading this disclosure, how to make and use alternative embodiments of the present invention that omit one or more of the tasks.

At task 410, terminal monitor 236 determines the identity of a software application component that is executing on terminal 130. In accordance with the illustrative embodiment of the present invention, the software application is a telephony application which comprises a telephony component and an instant messaging component. However it will be clear to those skilled in the art, after reading this disclosure, how to make and use alternative embodiments of the present invention in which any other application is analyzed (e.g. a word process, email client, etc.) Terminal monitor 236 determines which one of the two components is used.

In accordance with the illustrative embodiment of the present invention, terminal monitor 236 determines what components of the telephony application are used by examining log files that are recorded by the application. However, it will be clear to those skilled in the art, after reading this disclosure, how to make and use alternative embodiments of the present invention in which terminal monitor 236 uses alternative means to determine what application components are used. In one alternative embodiment of the present invention, terminal monitor 236 identifies one or more active processes and matches information about the processes (e.g. process name, files associated with the process, etc.) to a specific application component.

In another alternative embodiment of the present invention, terminal monitor 236 identifies patterns of resource consumption and matches these patterns to patterns that are known to be associated with specific application components. For example, and without limitation, the pattern of "25% CPU utilization" may be associated with the instant messenger component of the telephony application. Whereas the pattern of "50% CPU utilization" may be associated with the telephony component of the application. It will be clear to those skilled in the art how to recognize and relate patterns of resource consumption to specific software components.

At task 420, terminal monitor 236 determines the presence of a keyword in a file that is opened by a software application that is executing on terminal 130. In accordance with the illustrative embodiment of the present invention, the software application is a word processor, and the open file is a text document. However, it will be clear to those skilled in the art, after reading this disclosure, how to make and use alternative embodiments of the present invention in which the software application is any other software application that is capable of opening files (e.g. media player, another text editor, file compressing tool, etc.). Furthermore, it will be clear to those skilled in the art, after reading this disclosure, how to make and use alternative embodiments of the present invention in which the open files are of any other type (e.g. MP3, MPEG, JPEG, etc.)

In accordance with the illustrative embodiment of the present invention, terminal monitor 236 locates a document that has a lock placed on it and scans its content for the presence of one or more keywords. However, it will be clear to those skilled in the art, after reading this disclosure, how to make and use alternative embodiments of the present invention in which terminal monitor 236 locates documents that are open by using alternative means, such as, for example, and without limitation, monitoring system calls made by the software application, examining application log files which indicate what files are opened by the application. Moreover, in the alternative embodiments of the present invention in which the file is a media file, terminal monitor 236 uses voice recognition (or character/image recognition) technology to determine whether the keyword is present in the file.

At task 430, terminal monitor 236 identifies an address to which a software application is (or was) connected. The address is an Internet domain name, but it will be clear to those skilled in the art, after reading this disclosure, how to make and use alternative embodiments of the present invention in which the uniform identifier (URI) is any type of identifier (e.g. Internet Protocol (IP) address, SIP uniform resource identifier (URI), etc.). Furthermore, the software application is an Internet browser, but it will be clear to those skilled in the art, after reading this disclosure, how to make and use alternative embodiments of the present invention in which the software application is any other type of software application (e.g. FTP client, streaming media player, a server, chat client, email client, etc.). In accordance with the illustrative embodiment of the present invention, the address is determined by examining log files that are recorded by the Internet browser. However, it will be clear to those skilled in the art, after reading this disclosure, how to make and use alternative embodiments of the present invention in which the address is identified by alternative means, such as, for example, and without limitation, by examining network traffic, by monitoring the storage of cookies and other tokens on terminal 130, etc.

Figure 5:
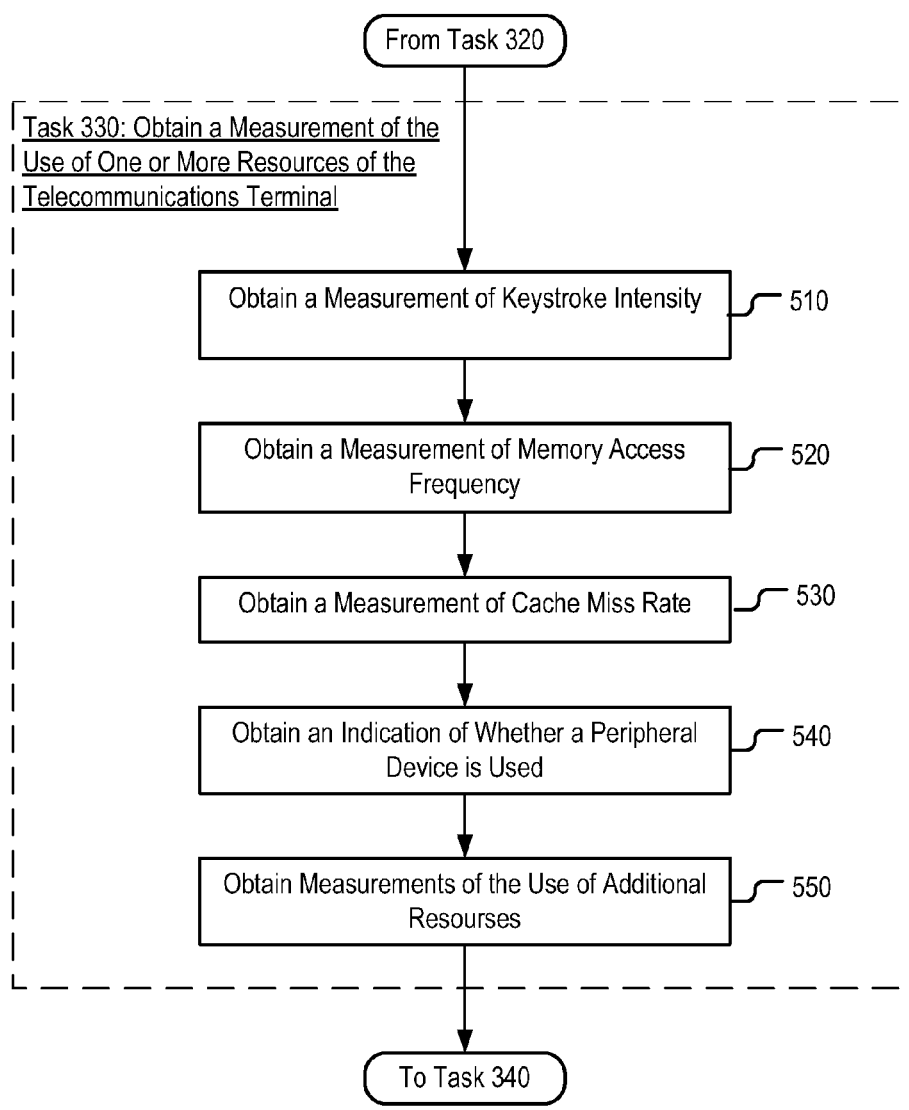
FIG. 5 depicts a flowchart of the execution of the salient subtasks associated with the performance of task 330.

FIG. 5 depicts a flowchart of the execution of the salient subtasks associated with the performance of task 330. It will be clear to those skilled in the art, after reading this disclosure, how to perform the tasks associated with FIG. 5 in a different order than represented or to perform one or more of the tasks concurrently. Furthermore, it will be clear to those skilled in the art, after reading this disclosure, how to make and use alternative embodiments of the present invention that omit one or more of the tasks.

The discussion with respect to FIG. 5 describes the taking of measurements of the use of resources of terminal 130. In accordance with the illustrative embodiment of the present invention, each measurement consists of five (5) samples taken four (4) seconds apart. However, it will be clear to those skilled in the art, after reading this disclosure, how to make and use alternative embodiments of the present invention in which any number of samples is taken (e.g. 1, 2, 3, 5, 100, 150, etc.) It will also be clear to those skilled in the art, after reading this disclosure, that each individual sample can be taken over any time window (i.e. the time period over which the data for an individual sample is collected can vary), such as, for example, and without limitation 1 second, 2 seconds, 3 seconds, 30 seconds, 1 minute, 15 minutes, 1 hour, etc. Furthermore, it will be clear to those skilled in the art that the time period between the different samples can be of any length (e.g. 1 second 10 seconds, 1 minute, 10 minutes, etc.). And still furthermore, it will be clear to those skilled in the art that the combination of number of samples, time over which each individual sample is taken, and time period between individual samples can be different for measurements of different resources.

At task 510, terminal monitor 236 obtains a measurement of the keystroke rate of terminal 130. A keystroke rate is the rate at which the user of terminal 130 presses the keys on the terminal's keyboard (e.g. 40 keys/minute, etc.).

At task 520, terminal monitor 236 obtains a measure of memory access frequency for terminal 130. In accordance with the illustrative embodiment of the present invention, the terminal measures the frequency at which information is requested from the permanent of storage of terminal 130. However, it will be clear to those skilled in the art, after reading this disclosure, how to make and use alternative embodiments of the present invention in which the terminal obtains alternative measurements, such as, for example, and without limitation, page fault rate, random access memory write rate, etc.

At task 530, terminal monitor 236 obtains a measurement of the cache miss rate for the processor of terminal 130. It will be clear to those skilled in the art, after reading this disclosure, how to make and use alternative embodiments of the present invention in which cache hit rate is measured instead.

At task 540, terminal monitor 236 determines whether a peripheral device is used by terminal 130. In accordance with the illustrative embodiment, the peripheral device is a scanner, but it will be clear to those skilled in the art, after reading this disclosure, how to make and use alternative embodiments of the present invention in which the use of another peripheral device is detected, such as, for example, and without limitation, printer, slide presentation remote control, microphone, video camera, audio speakers, headphones, etc.

At task 550, terminal monitor 236 obtains measurements of the use of additional hardware resources of terminal 130. In accordance with the illustrative embodiment the present invention, terminal monitor 236 determines processor temperature, video card (or GPU) temperature, video card memory use, whether video card 3D acceleration is used, whether surround sound capabilities of a sound adapter are used, sound adapter utilization, processor temperature, etc.

Figure 6:
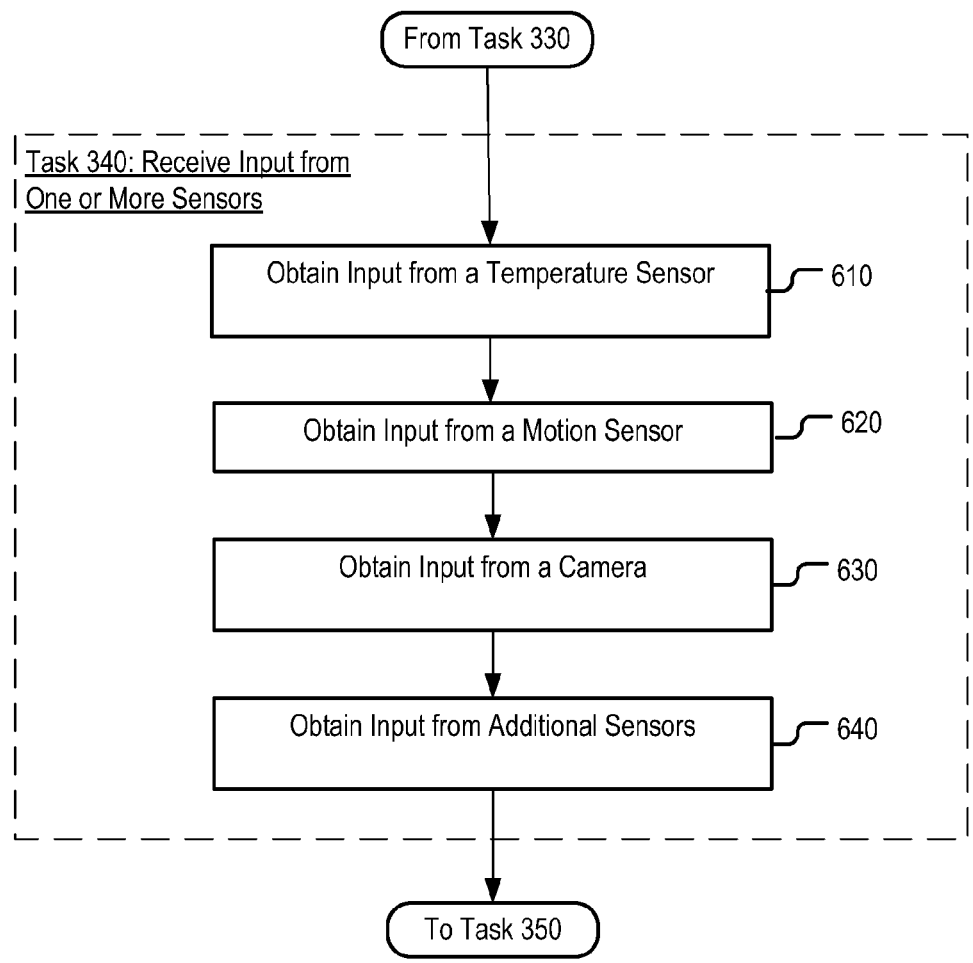
FIG. 6 depicts a flowchart of the execution of the salient subtasks associated with the performance of task 340.

FIG. 6 depicts a flowchart of the execution of the salient subtasks associated with the performance of task 340. It will be clear to those skilled in the art, after reading this disclosure, how to perform the tasks associated with FIG. 6 in a different order than represented or to perform one or more of the tasks concurrently. Furthermore, it will be clear to those skilled in the art, after reading this disclosure, how to make and use alternative embodiments of the present invention that omit one or more of the tasks.

The discussion with respect to FIG. 6 describes the taking of measurements from different sensors. In accordance with the illustrative embodiment of the present invention, each measurement consists of five (5) samples taken four (4) seconds apart. However, it will be clear to those skilled in the art, after reading this disclosure, how to make and use alternative embodiments of the present invention in which any number of samples is taken (e.g. 1, 2, 3, 5, 100, 150, etc.). It will also be clear to those skilled in the art, after reading this disclosure, that each individual sample can be taken over any time window (i.e. the time period over which the data for an individual sample is collected can vary), such as, for example, and without limitation, 1 second, 2 seconds, 3 seconds, 30 seconds, 1 minute, 15 minutes, 1 hour, etc. Furthermore, it will be clear to those skilled in the art that the time period between the different samples can be of any length (e.g. 1 second 10 seconds, 1 minute, 10 minutes, etc.). And still furthermore, it will be clear to those skilled in the art that the combination of: number of samples, time over which each individual sample is taken, and time period between individual samples can be different for measurements from different sensors.

At task 610, availability detector 237 obtains a temperature measurement from temperature sensor 251. It will be clear to those skilled in the art how to execute task 610.

At task 620, availability detector 237 obtains a measurement from motion sensor 252.

At task 630, availability detector 237 obtains input from camera 253. In accordance with the illustrative embodiment of the present invention, the camera input is used to determine whether a user is standing in the camera's range of vision. However it will be clear to those skilled in the art, after reading this disclosure, how to make and use alternative embodiments of the present invention in which availability detector 237 applies image recognition technologies such as, for example and without limitation, facial recognition, facial expression recognition, and gaze direction recognition.

At task 640, availability detector 237 obtains input from additional sensors, such as, for example, and without limitation, appliance sensors (i.e. sensors that detect whether a particular appliance, such as a kitchen stove, is running), barometric pressure sensors, humidity sensors, pressure sensors, sensors that measure physiological parameters (e.g. ECG, EEG, etc.), and others.

Figure 7:
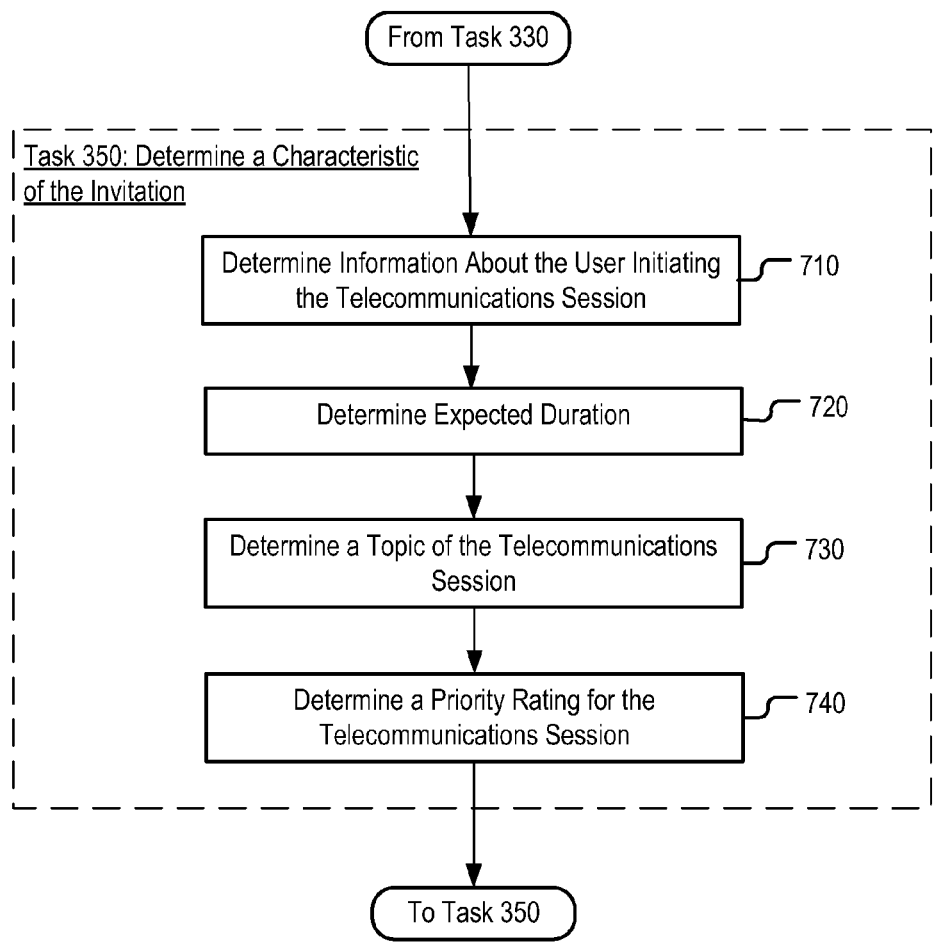
FIG. 7 depicts a flowchart of the execution of the salient subtasks associated with the performance of task 350.

FIG. 7 depicts a flowchart of the execution of the salient subtasks associated with the performance of task 350. It will be clear to those skilled in the art, after reading this disclosure, how to perform the tasks associated with FIG. 7 in a different order than represented or to perform one or more of the tasks concurrently. Furthermore, it will be clear to those skilled in the art, after reading this disclosure, how to make and use alternative embodiments of the present invention that omit one or more of the tasks.

At task 710, availability detector 237 obtains information about the user initiating the telecommunications session. In accordance with the illustrative embodiment of the present invention, availability detector 237 determines the endpoint identifier of the terminal from which the telecommunications session is initiated. However, it will be clear to those skilled in the art, after reading this disclosure, how to make and use alternative embodiments of the present invention in which availability detector 237 determines the identity of the person making the telephone call by using an identification technology, such as Caller ID or by doing a reverse telephone number lookup in a telephone directory.

It will also be clear to those skilled in the art, after reading this disclosure, how to make and use alternative embodiments of the present invention in which availability detector 237 determines additional information about the person initiating the telecommunications session, such as, for example, and without limitation, rank within a company (e.g. CEO, director of department, etc.), gender, age, employment status, social security number, etc. The alternative embodiments of the present invention obtain the additional information by performing a database search with a search key that is based on the endpoint identifier of terminal 110. However, it will be clear to those skilled in the art, after reading this disclosure, how to make and use further alternative embodiments of the present invention in which the additional information is contained in the invitation itself or contained in a separate message that is received by availability detector 237.

Furthermore, it will be clear to those skilled in the art, after reading this disclosure, how to make and use alternative embodiments of the present invention, in which a relationship between the user initiating the telecommunications session and the user of terminal 130 is obtained or determined (e.g. the caller is the supervisor of the user of terminal 130, the caller is a relative of the user of terminal 231-1, etc.). In some alternative embodiments of the present invention, the relationship information is received at terminal 130 along with the invitation to participate in a telecommunications session. In other embodiments of the present invention, the relationship between the caller and the user of terminal 130 is derived from the identity information of the caller and tables that relate the caller to the user (e.g. employee records, family records, etc.).

At task 720, availability detector 237 determines the expected duration of the telecommunications session. Availability detector 237 searches a call log for information about the duration of past telecommunications sessions between terminal 130 and terminal 110 and calculates the expected duration of the telecommunications session for which invitation is received. In accordance with the illustrative embodiment of the present invention, the expected duration is the average of the n most recent telecommunications sessions, where n is an integer.

Furthermore, it will be clear to those skilled in the art, after reading this disclosure, how to make and use alternative embodiments of the present invention in which the expected duration is contained in the invitation itself (e.g. the content of the ANI field or an equivalent is overwritten, etc.). And still furthermore, it will be clear to those skilled in the art, after reading this disclosure, how to make and use alternative embodiments of the present invention in which the expected duration is received at terminal 130 in a message that is separate from the invitation.

At task 730, availability detector 237 determines the topic of the telecommunications session. In accordance with the illustrative embodiment of the present invention, an indication of the topic is contained in the invitation itself (e.g. the content of the ANI field or an equivalent is overwritten, etc.). However, it will be clear to those skilled in the art, after reading this disclosure, how to make and use alternative embodiments of the present invention in which an indication of the topic is received in a message that is separate from the invitation.

At task 740, availability detector 237 determines a priority rating for the telecommunications session. In accordance with the illustrative embodiment of the present invention, one of three ratings is chosen: "important," "extremely important," and "not important." However, it will be clear to those skilled in the art, after reading this disclosure, how to make and use alternative embodiment of the present invention in which the space of possible ratings is either larger or smaller.

In accordance with the illustrative embodiment of the present invention, an indication of the priority rating is contained in the invitation itself (e.g. the content of the ANI field or an equivalent is overwritten, etc.). However, it will be clear to those skilled in the art, after reading this disclosure, how to make and use alternative embodiments of the present invention in which an indication of the priority rating is received in another message that is separate from the invitation. Furthermore, it will be clear to those skilled in the art, after reading this disclosure, how to make and use alternative embodiments of the present invention in which the importance rating is determined by availability detector 237 on the basis of information received at tasks 710 through 730 (e.g. if the CEO calls, the priority rating is set to "extremely important"; if the topic is accounting, the priority rating is set to "important").

Figure 8:
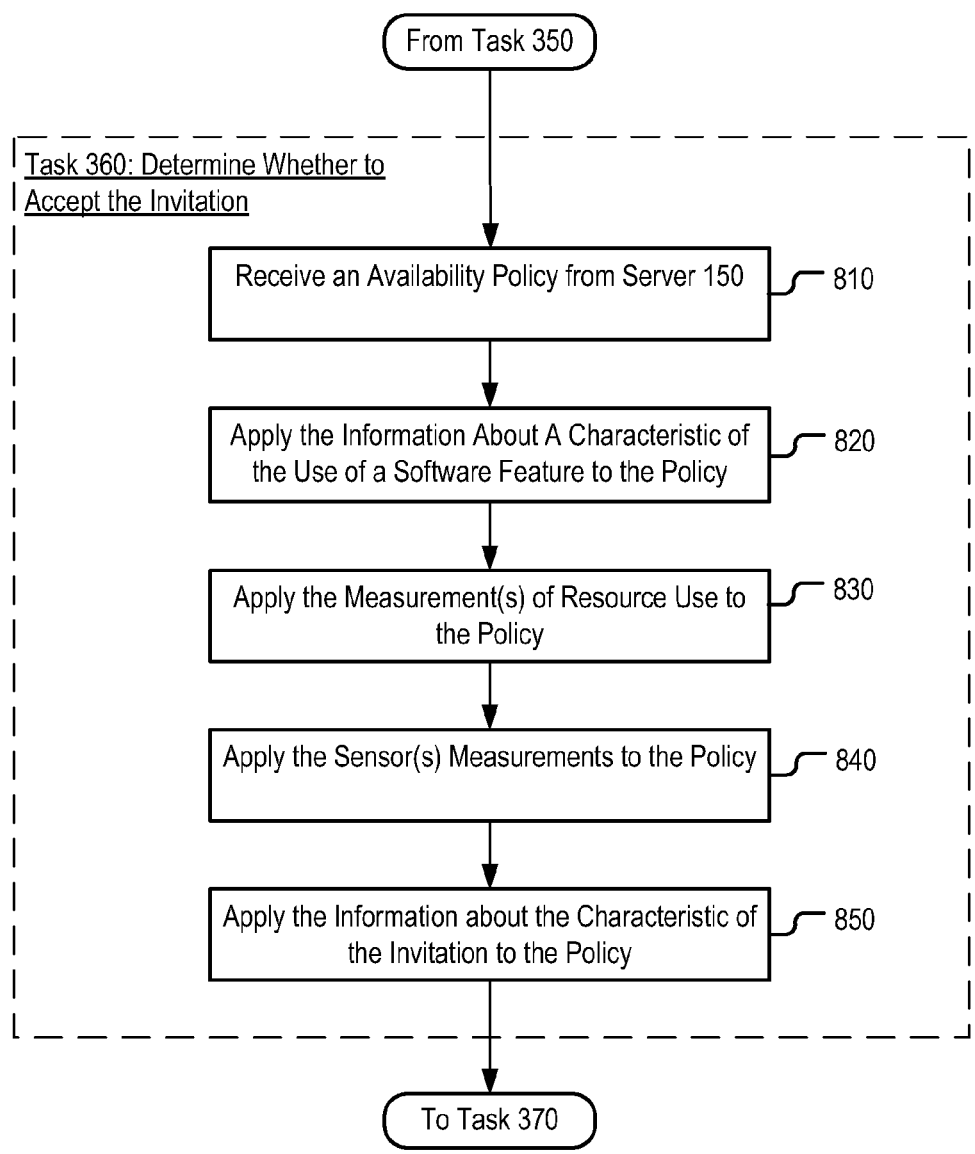
FIG. 8 depicts a flowchart of the execution of the salient subtasks associated with the performance of task 360.

FIG. 8 depicts a flowchart of the execution of the salient subtasks associated with the performance of task 360. It will be clear to those skilled in the art, after reading this disclosure, how to perform the tasks associated with FIG. 8 in a different order than represented or to perform one or more of the tasks concurrently. Furthermore, it will be clear to those skilled in the art, after reading this disclosure, how to make and use alternative embodiments of the present invention that omit one or more of the tasks.

At task 810, availability detector 237 receives an availability policy from server 150. As previously noted, for the purposes of this Specification, the term "availability policy" is defined as a set of one or more rules which determine when a user is available for telecommunications. In accordance with the illustrative embodiment of the present invention, the policy is received in an extensible markup language (XML) file, but it will be clear to those skilled in the art, after reading this disclosure, how to make and use alternative embodiments of the present invention in which the policy is represented in any other form, such as, for example, a text file, a sequence of numbers, etc. Although, in accordance with the illustrative embodiment of the present invention, the policy is obtained from a server, it will be clear to those skilled in the art, after reading this disclosure, how to make and use alternative embodiments of the present invention in which the policy is stored on terminal 130.

More specifically, at task 810, the present invention receives an availability policy which comprises four rules for determining whether a user is available. These rules are:

i. "user is unavailable if the weighed sum of availability scores assigned to web sites which the user recently visited is below fifty-five (55),"

ii. "user is unavailable if the weighted sum of the five most recent samples of the user's keystroke rate exceeds one-hundred and thirty (130),"

iii. "user is unavailable if the temperature in the office of the user is below fifty-five degrees Fahrenheit (55 F)," and iv. "user is available if the CEO of a company calls."

In accordance with the illustrative embodiment of the present invention, the availability policy rules specify whether a user is to accept an incoming invitation to participate in a telecommunications session. However, it will be clear to those skilled in the art, after reading this disclosure, how to make and use alternative embodiments of the present invention in which the availability policy rules specify other aspects of a user's availability, such as, for example, and without limitation, an alternative communication medium, alternative time to call, time delay for which the far-end party is to be put on hold, etc.

In the alternative embodiments of the present invention in which availability policy rules are used to select a preferred medium of communication on which the user is available, the rules depend on one or more of a characteristic of the use of a software application component, a measurement of the use of one or more resources of terminal 130, input from one or more sensors, and a characteristic of the invitation. Examples of such rules include:

i. "notify far-end party that text is a preferred medium of communication if the keystroke rate of the user of terminal 130 exceeds eighty (80) characters per minute,"

ii. "notify far-end party that voice is a preferred medium of communication if the user is using the chat component of a telephony application that is running on availability detector 237."

In the alternative embodiments of the present invention in which the incoming invitation to participate in a telecommunications session is accepted, but put on hold, the time period for which the session is held idle is determined in accordance with one or more availability policy rules. The availability policy rules, in these alternative embodiments, depend on one or more of: a characteristic of the use of a software application component, a measurement of the use of one or more resources of terminal 130, input from one or more sensors, and a characteristic of the invitation. Examples of such rules include:

i. "put the session on hold for n minutes, if the measured keystroke rate is between fifty (50) and eighty (80) strokes per minute,"

ii. "put the session on hold until the keystroke falls below a threshold (e.g. 50 keystrokes),"

iii. "put the session on hold until a input from one or more sensors falls below a threshold (e.g. motion sensor indicates that a user has stopped moving intensely)," and vi. "put the session on hold until the user of terminal 130 stops using a specific software application component."

It will be clear to those skilled in the art, after reading this disclosure, how to make and use alternative embodiments of the present invention in which tasks 330 through 360 are executed repeatedly, after the far-end party is put on hold, until availability detector 237 determines that a condition which determines whether a user is to be taken off hold has been fulfilled.

Furthermore, it will be clear to those skilled in the art, after reading this disclosure, how to make and use alternative embodiments of the present invention, in which terminal 130 initially declines the invitation to participate the telecommunications session from terminal 110, but continues to execute tasks 330 through 360 repeatedly until the user of terminal 130 becomes available, as determined according to an availability rule. When the user becomes available, terminal 130 initiates a new telecommunications session with terminal 110.

For example, and without limitation, in one alternative embodiment of the present invention, tasks 330 through 360 are executed until the user's keystroke intensity falls below a threshold, such as fifty keystrokes per minute. In this alternative embodiment of the present invention, the availability rule provides that a user is available if the user's keystroke rate is under fifty keystrokes per minute. Thus, when the user's keystroke rate falls below the threshold, terminal 130 initiates a new telecommunications session with terminal 110.

In the alternative embodiments of the present invention in which availability policy rules are used to determine an alternative time for the far end party to call, the rules depend on one or more of: a characteristic of the use of a software application component, a measurement of the use of one or more resources of terminal 130, input from one or more sensors, and a characteristic of the invitation. Examples of such rules include:

i. "if cache miss rate exceeds fifty percent (50%), ask far-end party to call back in ninety (90) minutes,"

ii. "if the movie player component of a multimedia player application is used, ask far-end party to call in a predetermined period of time (e.g. 120 minutes)."

In accordance with the alternative embodiments of the present invention, the call-back time period is provided in the policy rule used to determine availability. However, it will be clear to those skilled in the art, after reading this disclosure, how to make and use alternative embodiments of the present invention in which the call-back time period is determined according to appointment information that is stored on terminal 130 (e.g. information stored by calendar applications, etc.).

Although, in accordance with the illustrative embodiment of the present invention, the availability policy rules are neutral with respect to the time at which the telecommunications session is received or the medium of the telecommunications session, it will be clear to those skilled in the art, after reading this disclosure, how to make and use alternative embodiments of the present invention in which the rules depend on the time at which the invitation to participate on the telecommunications session is received or the medium of the telecommunications session. Examples of such rules include:

i. "user is unavailable if the invitation to participate in a telecommunications session is received within a specific time period;"

ii. "user is available if the medium for the telecommunications session is text;"

iii. "user is unavailable if the medium for the telecommunications session is voice."

At task 820, availability detector 237 applies the first rule to the information at task 320. Although, the first rule depends on the recent web site visits, it will be clear to those skilled in the art, after reading this disclosure, how to make and use alternative embodiments of the present invention in which the first rule depends on any type of information that is received at task 320 (e.g. use of specific components of software, presence of keywords, etc.). Task 820 is further described in the discussion with respect to FIG. 9 and FIG. 10.

At task 830, availability detector 237 applies the second rule to the information obtained at task 330. Although, the second rule depends on keystroke intensity measurements, it will be clear to those skilled in the art, after reading this disclosure, how to make and use alternative embodiments of the present invention in which the second rule depends on any type of information that is received at task 330 (e.g. measurements of memory access rate, cache miss rate, information whether a peripheral device is used, etc.). Task 830 is further described in the discussion with respect to FIG. 11.

At task 840, availability detector 237 applies the third rule to the information that is received at task 340. Although, the third rule depends on a temperature measurement, it will be clear to those skilled in the art, after reading this disclosure, how to make and use alternative embodiments of the present invention in which the third rule depends on any type of information that is collected at task 340 (e.g. motion sensor input, camera input, etc.). Task 840 is further described in the discussion with respect to FIG. 12.

At task 850, availability detector 237 applies the fourth rule to the information that is obtained at task 350. In accordance with the rule, if the user which initiated the telecommunications session is the CEO of a company, availability detector 237 accepts the invitation. Although, the fourth rule depends on the position of the calling party within a company, it will be clear to those skilled in the art, after reading this disclosure, how to make and use alternative embodiments of the present invention in which the fourth rule depends on any information that is obtained at task 350. For example, and without limitation, such alternative rules include:
  i. "user is always available if the priority rating of the invitation is "extremely important," and
  ii. "user is always available if the expected duration for the telecommunications session is less than a predetermined threshold (e.g. 5 minutes)"

It will also be clear to those skilled in the art, after reading this disclosure, how to make and use alternative embodiments of the present invention in which the rule depends on a relationship, which is determined at task 710, between the calling party and the user of terminal 130. For example, and without limitation, such rules include:
  i. "user is always available if a relative of the user calls"
  ii. "user is always available if someone who is higher up in the user's company calls"

Figure 9:
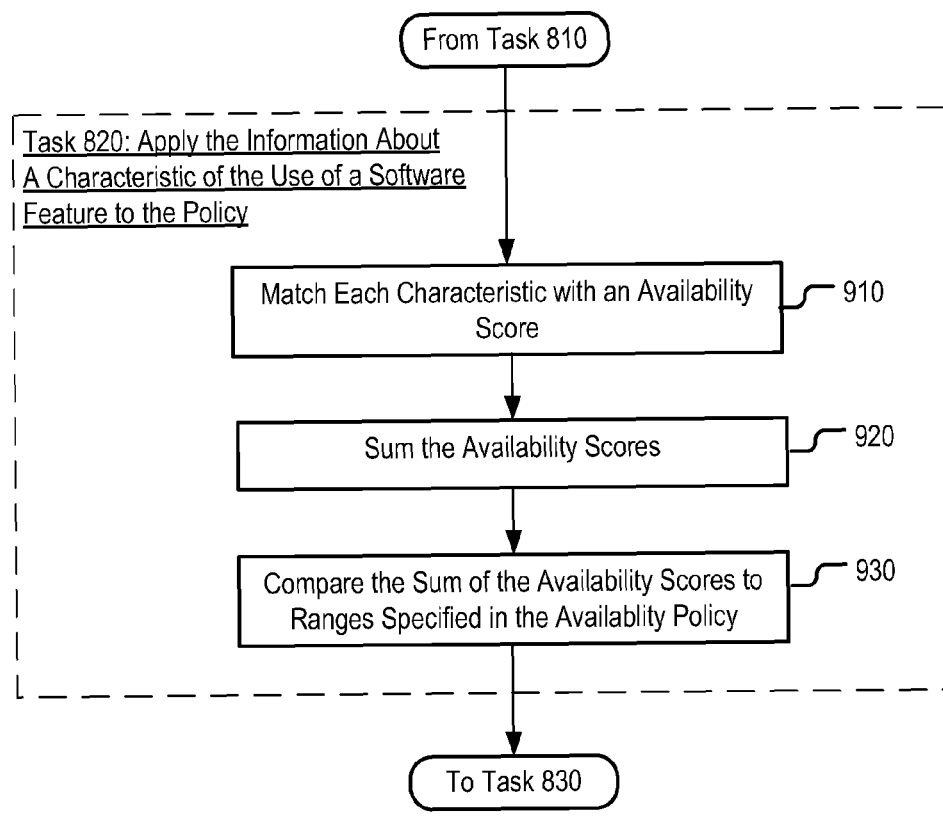
FIG. 9 depicts a flowchart of the execution of the salient subtasks associated with the performance of task 820.

FIG. 9 depicts a flowchart of the execution of the salient subtasks associated with the performance of task 820. It will be clear to those skilled in the art, after reading this disclosure, how to perform the tasks associated with FIG. 9 in a different order than represented or to perform one or more of the tasks concurrently. Furthermore, it will be clear to those skilled in the art, after reading this disclosure, how to make and use alternative embodiments of the present invention that omit one or more of the tasks.

At tasks 910 through 930, availability detector 237 applies the first policy rule that received at task 810. The first policy rule provides that a user is unavailable if the weighed sum of availability scores assigned to web sites which the user recently visited is less than fifty-five (55).

Availability scores are numbers which are used in determining whether the user of terminal 130 is available to participate in telecommunications. In accordance with the illustrative embodiment of the present invention, the availability scores are contained in the indication of the policy received at task 810 (e.g. the XML file), however, those skilled in the art will readily recognize, after reading this disclosure, how to make and use alternative embodiments of the present invention in which the availability scores are separated from the availability policy, such as, for example, and without limitation, embodiments in which the availability scores are stored on terminal 130 or on a remote server.

At task 910, availability detector 237 matches a characteristic with an availability score. In accordance with a first illustrative embodiment of the present invention, the following set of availability scores is made available for uniform resource identifiers (URIs) that were visited by terminal 130:

TABLE 1

Availability Scores Assigned to Uniform Resource Identifiers

| Uniform Resource Identifier (URI) | Availability Score |
|---|---|
| Movies.com ™ | 10 |
| Bloomberg.com ™ | 40 |
| Internal_document_repository | 85 |

As noted, the availability score is an indication of the likelihood that the user of terminal 130 is not available to accept the incoming invitation. In accordance with the illustrative embodiment of the present invention, the magnitude of the availability score is inversely proportional to the probability that the user is available to respond to the invitation received at task 310. Furthermore, in accordance with the illustrative embodiment of the present invention, "Movies.com™" is assigned a low availability score. The rationale for assigning the low score is that Movies.com™ is a website that is usually viewed for personal entertainment. In contrast, the internal document repository, in this illustrative embodiment, is a document storage location which is used strictly for business. If the user is visiting the document repository, he or she is most likely to be engaged in performing tasks related to the user's employment. For this reason, the internal document repository is assigned a high availability score.

In accordance with a first alternative embodiment of the present invention, the following availability scores are assigned to different software application components:

TABLE 2

Availability Scores Assigned to Software application components

| Software application component | Availability Score |
|---|---|
| Skype ™ instant messenger component | 15 |
| Outlook ™ calendar | 85 |
| Skype ™ Directory component | 10 |

In accordance the first alternative embodiment of the present invention, the Skype™ instant messenger component is accorded a low availability score and the Outlook™ calendar component is accorded a high availability score. The rationale for this assignment is that Internet chat is usually conducted for personal entertainment and not for work, while adding and editing appointments in a calendar is considered part of one's employment duties.

In accordance with a second alternative embodiment of the present invention, the following availability scores are assigned to keywords that are found in documents that are opened for editing:

TABLE 3

Availability Scores Assigned to Keywords

| Keywords | Availability Score |
|---|---|
| "LOL" | 15 |
| "fiscal year" | 40 |
| "project deadline" | 85 |

In accordance with the second embodiment of the present invention, the word "LOL" is assigned a low priority score. "LOL" is an abbreviation for "laughing out loud" and is a common element of Internet slang. When this word is present in a document, the user of terminal 130 is likely engaged in a personal conversation. Consequently, the keyword "LOL" is assigned a low availability score.

In accordance with the second alternative embodiment of the present invention, two types of documents are scanned for keywords by availability detector 237:
  i. documents which are open by the user of terminal 130 for editing, and
  ii. documents which are open by a software application for editing as a result of a user's interaction with the software application, such as a message log which is open as a consequence of a user sending an instant message, possibly, without the user being aware of its opening.

However, it will be clear to those skilled in the art, after reading this disclosure, how to make and use alternative embodiments of the present invention in which only one of the two types of documents is scanned. Furthermore, it will be clear to those skilled in the art, after reading this disclosure, how to make and use alternative embodiments of the present invention in which any characteristic of the use of a component of software application that is obtained at task 320 is matched with an availability score.

At task 920, availability detector 237 calculates the sum of the availability scores identified at task 910. It will be clear to those skilled in the art, after reading this disclosure, how to make and use alternative embodiments of the present invention in which availability detector 237 calculates an alternative number, such as, for example, and without limitation, a weighted sum, weighted average, the average of the scores, and others.

At task 930, availability detector 237 matches the calculated sum to a predetermined range defined in the policy received at task 810. In accordance with the illustrative embodiment of the present invention, the policy provides that if the sum is less than fifty-five (55), the user of terminal 130 is available to accept the invitation to participate in a telecommunications session.

Figure 10:
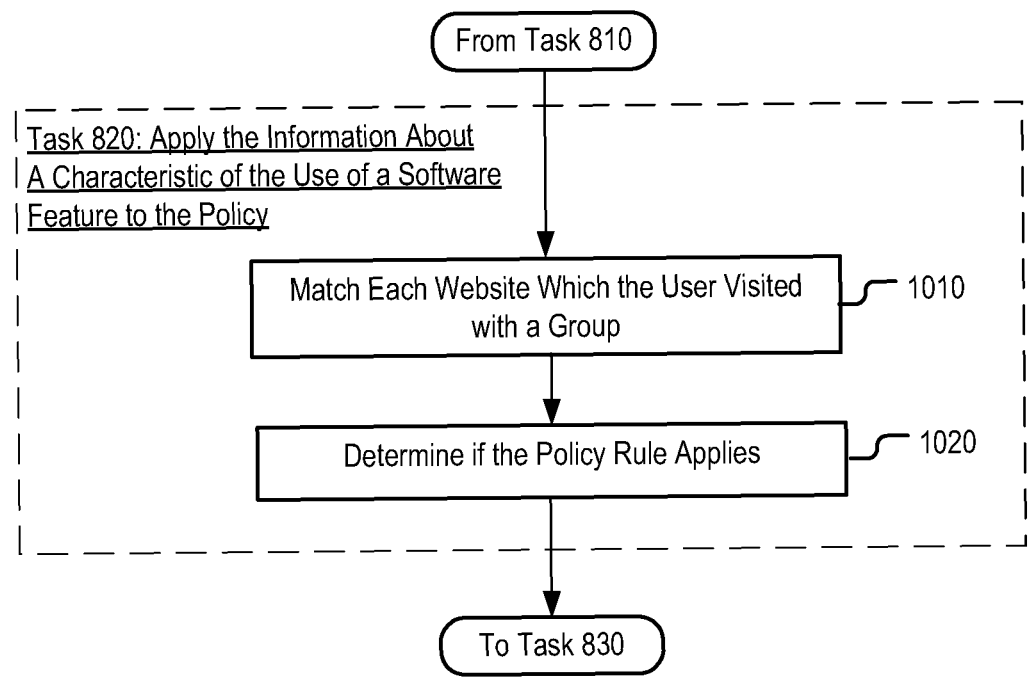
FIG. 10 depicts a flowchart of the execution of the salient subtasks associated with the performance of task 820 as performed by another illustrative embodiment of the present invention.

FIG. 10 depicts a flowchart of the execution of the salient subtasks associated with the performance of task 820 as performed by another illustrative embodiment of the present invention. It will be clear to those skilled in the art, after reading this disclosure, how to perform the tasks associated with FIG. 10 in a different order than represented or to perform one or more of the tasks concurrently. Furthermore, it will be clear to those skilled in the art, after reading this disclosure, how to make and use alternative embodiments of the present invention that omit one or more of the tasks.

At tasks 1010 and 1020, availability detector 237 applies a policy rule. The policy rule provides that a user is unavailable if the number of websites from a "business" group, which the user visited, is more than or equal to the number of visited websites from a "personal entertainment" group. In accordance with this illustrative embodiment of the present invention, the websites visited are classified into groups. In accordance with the illustrative embodiment of the present invention, the availability group definitions are contained in the policy received at task 810 (e.g. the XML file), however, those skilled in the art will readily recognize, after reading this disclosure, how to make and use alternative embodiments of the present invention in which the group definitions are stored on terminal 130 or on a remote server.

At task 1010, availability detector 237 determines the groups for the last three web sites that were most recently visited by an Internet browser executing on the terminal. The three websites are "Movies.com™," "Bloomberg.com™," and "internal document repository." The group definitions for the illustrative embodiment of the present invention are listed below:

TABLE 4

Web Site Group Definitions

| Business Websites | Entertainment Websites | News Websites |
|---|---|---|
| Internal document repository | Youtube.com ™ | Bloomberg.com ™ |
| Corporation web site | Movies.com ™ | Cnn.com ™ |
| A client web site | Netflix.com ™ | News.com ™ |
| Another client's website | Cinema.com ™ | bbc.com ™ |

It will be clear to those skilled in the art, after reading this disclosure, how to make and use alternative embodiments of the present invention in which the group definitions are different. Those skilled in the art will readily recognize, after reading this disclosure that the group definitions depend on the application for which the invention is used.

Additionally, it will be clear to those skilled in the art, after reading this disclosure, how to make and use alternative embodiments of the present invention in which any type of information obtained at task 320 is classified in groups. For example, and without limitation, in one alternative embodiment of the present invention, different application components are classified in the following way:

TABLE 5

Software application component Group Definitions

| Business Components | Entertainment Components |
|---|---|
| Skype ™ Voice Call Component | Skype ™ Video Call Component |
| MS Word ™ document editor | MS Word ™ Blog Plug in |
| Internet Browser Web Conferencing Component | Internet Browser Animation Component |

At task 1020, availability detector 237 determines whether the policy rule applies. Since Movies.com™ belongs to the entertainment group, the internal document repository belongs to the business group, and Bloomberg.com™ belongs to neither of the "business" and "entertainment groups," the number of "business" websites visited by the user is more than or equal to the number of "entertainment" web sites. Therefore, in accordance with the availability policy rule of this embodiment, the user is found available to participate in a telecommunications session.

Figure 11:
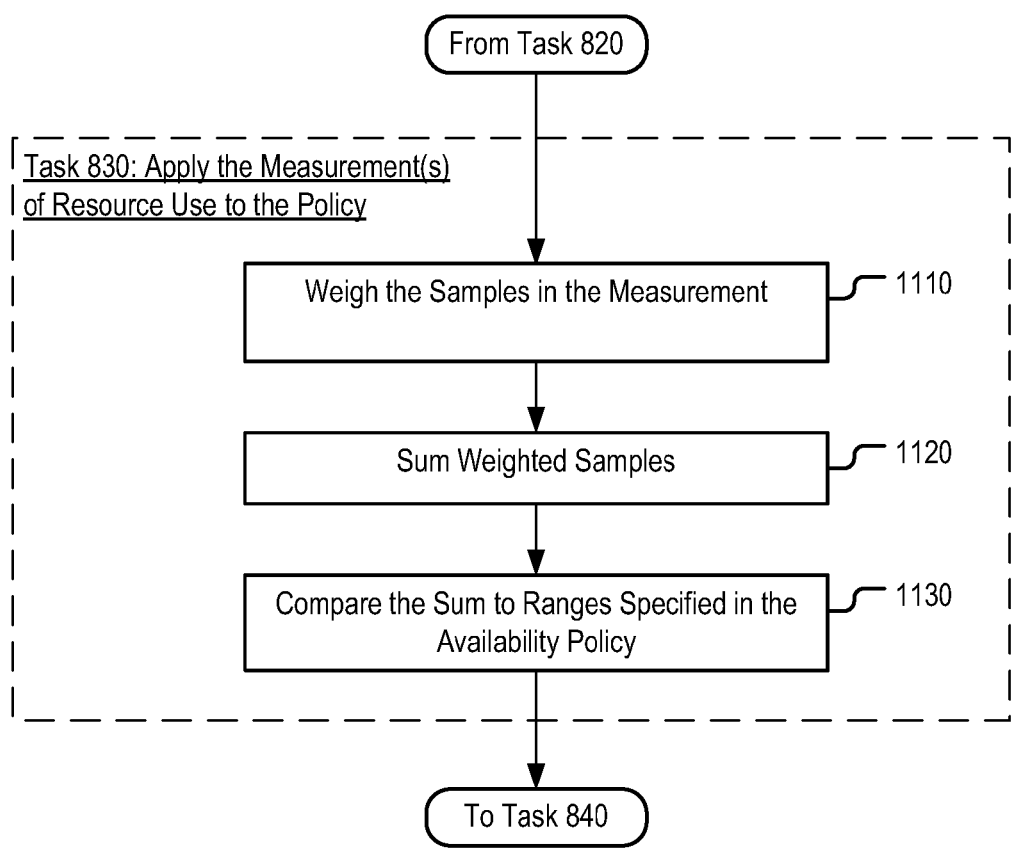
FIG. 11 depicts a flowchart of the execution of the salient subtasks associated with the performance of task 830.

FIG. 11 depicts a flowchart of the execution of the salient subtasks associated with the performance of task 830. It will be clear to those skilled in the art, after reading this disclosure, how to perform the tasks associated with FIG. 11 in a different order than represented or to perform one or more of the tasks concurrently. Furthermore, it will be clear to those skilled in the art, after reading this disclosure, how to make and use alternative embodiments of the present invention that omit one or more of the tasks.

At tasks 1110 through 1130, availability detector 237 applies the second policy rule received at task 810 to the information received at task 330. The second policy rule provides that a user is unavailable if the weighted sum of the five most recent samples of the user's keystroke rate exceeds one-hundred and thirty (130).

At task 1110, availability detector 237 weights the samples in the measurements of the use of resources of terminal 130 which were obtained at task 330. In accordance with the illustrative embodiment of the present invention, availability detector 237 receives a measurement of the rate at which keys on its keyboard are struck (i.e. keystroke rate). Availability detector 237 receives the data samples contained in the first two rows of Table 4:

TABLE 6

Keystroke Samples and Corresponding Weight Values

| | Sample (keystrokes/minute) | | | | |
|---|---|---|---|---|---|
| | 45 | 80 | 55 | 32 | 65 |
| Time at Which the Sample is Taken | $t_0$ | $t_1$ | $t_2$ | $t_3$ | $t_4$ |
| Weight Coefficient | 1 | .85 | .75 | .60 | .45 |

In accordance with the illustrative embodiment of the present invention, each sample is multiplied to the weight coefficient in order to derive the weighted value of this sample. The samples are weighted according to the time at which they are taken (e.g. the more recent samples are weighted less). It will be clear to those skilled in the art how to assign appropriate weight values. Furthermore, it will be clear to those skilled in the art, after reading this disclosure, how to make and use alternative embodiments of the present invention in which the samples are not weighted.

At task 1120, availability detector 237 calculates the sum of the weighted samples.

At task 1130, availability detector 237 matches the calculated sum to a predetermined range defined in the policy received at task 810. In accordance with the illustrative embodiment of the present invention, the policy provides that if the sum of the weighted keystroke rate samples is less than 130, the user of terminal 130 is available to accept the invitation to participate in a telecommunications session. Although, the policy is based on a plurality of keystroke rate samples, it will be clear to those skilled in the art, after reading this disclosure, how to make and use alternative embodiments of the present invention in which the policy depends on a single sample (e.g. "user is unavailable if keystroke rate is greater than eighty (80) characters per minute), on the weighted average of the samples or any other combination of the samples.

Although, the policy rule of the illustrative embodiment of the present invention depends on keystroke rate, it will be clear to those skilled in the art, after reading this disclosure, how to make and use alternative embodiments of the present invention in which the availability policy rule depends on the use of other resources measured at task 330 (e.g. both keystroke rate and cache miss rate, etc.). Examples of such rules are:

i. "user is unavailable when cache miss rate exceeds fifty percent (50%);"

ii. "user is available if less than ten (10) read requests to memory (either permanent or volatile) are made in the past minute;"

iii. "user is unavailable if a scanner connected to terminal 130 is being used at the time at which the invitation to participate in a telecommunications session is received."

It will be clear to those skilled in the art, after reading this disclosure how to make and use alternative embodiments of the present invention in which the ranges for availability and unavailability differ from the illustrative embodiment. It will be clear to those skilled in the art, after reading this disclosure, how to assign values to the ranges. Furthermore, it will be clear to those skilled in the art, after reading this disclosure, how to make and use alternative embodiments of the present invention, in which a third range is specified and when the sum falls into the third range, a message is transmitted from terminal 130 to terminal 110 asking the user of terminal 110 to call back in a predetermined period of time (e.g. 30 minutes).

Figure 12:
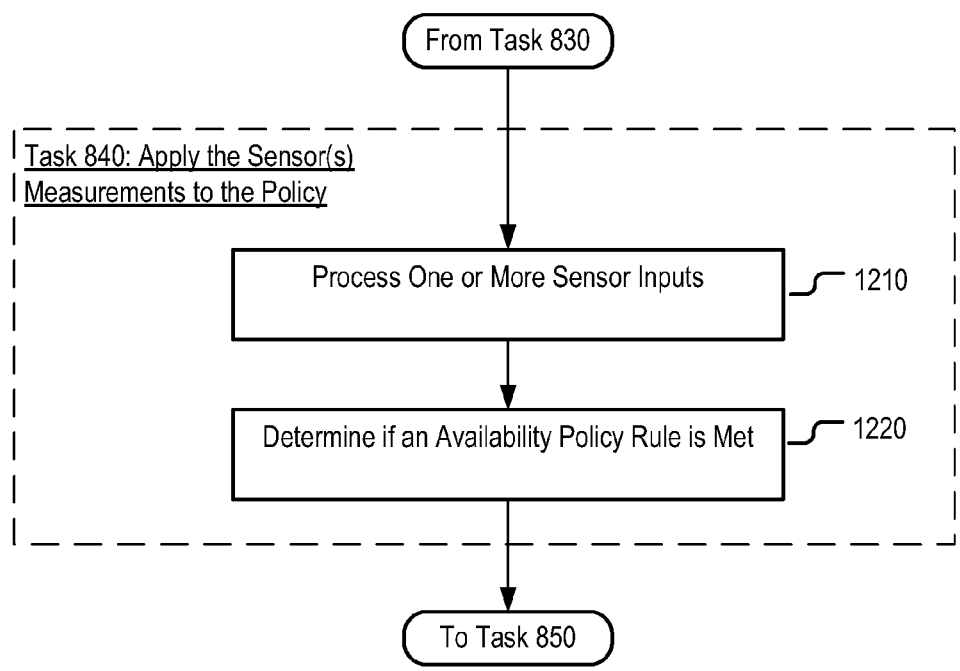
FIG. 12 depicts a flowchart of the execution of the salient subtasks associated with the performance of task 840.

FIG. 12 depicts a flowchart of the execution of the salient subtasks associated with the performance of task 840. It will be clear to those skilled in the art, after reading this disclosure, how to perform the tasks associated with FIG. 12 in a different order than represented or to perform one or more of the tasks concurrently. Furthermore, it will be clear to those skilled in the art, after reading this disclosure, how to make and use alternative embodiments of the present invention that omit one or more of the tasks.

At tasks 1210 through 1230, availability detector 237 applies the third policy rule received at task 810 to the information received at task 340. The third policy rule provides that a user is unavailable if the temperature in the office of the user is below fifty-five degrees Fahrenheit (55 F).

At task 1210, availability detector 237 processes the sensor input received at task 340. In accordance with the illustrative embodiment of the present invention, availability detector 237 digitizes (when analog signal is received) and normalizes the sensor data received at task 340. Although, in accordance with the illustrative embodiment of the present invention, input from a temperature sensor is processed, it will be clear to those skilled in the art, after reading this disclosure, how to make and use alternative embodiments of the present invention in which input from other sensors (e.g. motion sensors, physiological sensors, humidity sensors, etc.) is processed in the same fashion.

In accordance with one alternative embodiment of the present invention, availability detector 237 processes the camera input received at task 630 to determine the mood of the user. Specifically, the terminal uses a mood detector that employs facial recognition. However, it will be clear to those skilled in the art, after reading this disclosure, how to make and use alternative embodiments of the present invention in which input from physiological sensors (e.g. ECG and EEG) is also used in assessing the mood of the user of terminal 130.

At task 1220, availability detector 237 determines whether the input from a temperature sensor received at task 340 indicates that the temperature is below fifty-five degrees Fahrenheit (55 F).

In accordance with the alternative embodiment of the present invention, availability detector 237 applies the results from the mood detection to a policy which relates users' mood to their availability. Furthermore, in accordance with the alternative embodiment of the present invention, the policy provides that the incoming invitation should be accepted only when the mood detection concludes that the user of terminal 130 is in a positive mood.

Figure 13:
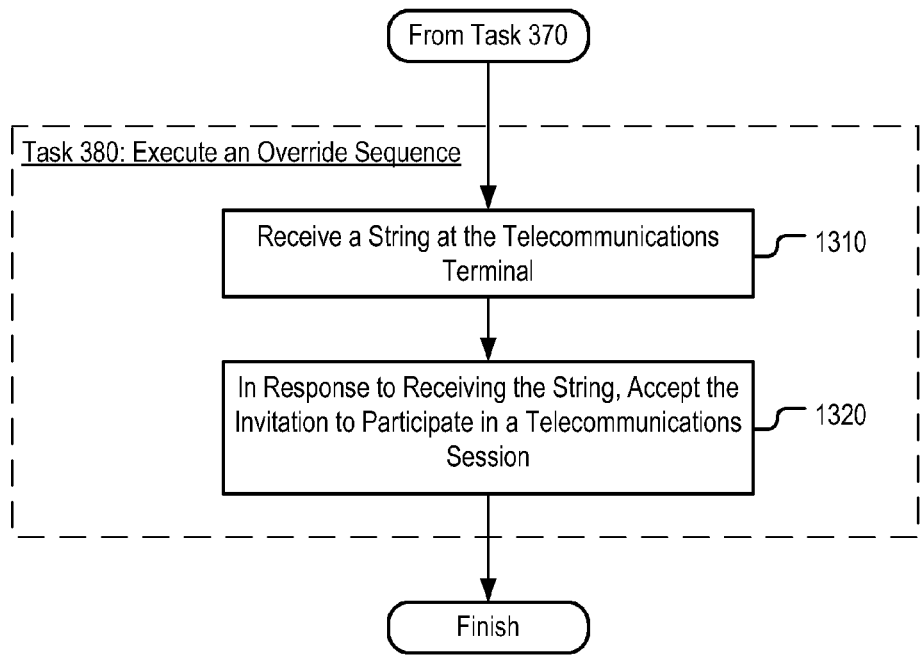
FIG. 13 depicts a flowchart of the execution of the salient subtasks associated with the performance of task 380.

FIG. 13 depicts a flowchart of the execution of the salient subtasks associated with the performance of task 380. It will be clear to those skilled in the art, after reading this disclosure, how to perform the tasks associated with FIG. 13 in a different order than represented or to perform one or more of the tasks concurrently. Furthermore, it will be clear to those skilled in the art, after reading this disclosure, how to make and use alternative embodiments of the present invention that omit one or more of the tasks.

At task 1310, terminal 130 receives a string from terminal 110. In accordance with the illustrative embodiment of the present invention, the string is alphanumerical, but it will be clear to those skilled in the art, after reading this disclosure, that the string can be of any type (e.g. numerical, etc.)

At task 1320, availability detector 237 compares the received to the string to a second string which is stored on terminal 130. If the two strings match, availability detector 237 causes terminal 130 to accept the invitation received at task 310. It will be clear to those skilled in the art, after reading this disclosure, how to make and use alternative embodiments of the present invention in which the string is stored on a remote server and not on terminal 130. Furthermore, it will be clear to those skilled in the art, after reading this disclosure, how to make and use alternative embodiments of the present invention in which the second string is specified by the policy received at task 810. And still furthermore, it will be clear to those skilled in the art, after reading this disclosure, how to make and use alternative embodiments of the present invention in which the policy received at task 810 provides whether availability detector 237 should accept the call even if the two strings match (i.e. the policy provides whether the override component of the present invention is enabled).

It is to be understood that the disclosure teaches just examples of the illustrative embodiments and that many variations of the invention can easily be devised by those skilled in the art after reading this disclosure and that the scope of the present invention is to be determined by the following claims.

What is claimed is:

1. A method comprising:
   receiving, at a telecommunications terminal, an invitation to participate in a telecommunications session, wherein:
   i. conduct of the telecommunications session requires the telecommunications terminal to utilize a first component of a software application, and
   ii. the software application is executing on the telecommunications terminal;
   obtaining, at the telecommunications terminal, a first characteristic of use of a second component of the software application;
   transmitting, from the telecommunications terminal, a rejection of the invitation based on the first characteristic;
   obtaining, at the telecommunications terminal, a second characteristic of use of the second component of the software application; and
   initiating a telecommunications session from the telecommunications terminal when the second characteristic of use of the second component of the software application meets a criterion.

2. The method of claim 1, further comprising receiving, at the telecommunications terminal, an indication of an availability policy, and wherein the rejection of the invitation is further based on the availability policy.

3. The method of claim 1, wherein the first characteristic is a Uniform Resource Identifier (URI) to which the software application established a connection.

4. The method of claim 1, wherein the first characteristic comprises a presence of a keyword.

5. The method of claim 1, wherein the first characteristic comprises an access permission for a document that is open for editing by the software application.

6. The method of claim 1, wherein the rejection is also based on a characteristic of the invitation to participate in the telecommunications session.

7. The method of claim 1, further comprising:
   receiving a first string at the telecommunications terminal; and
   in response to receiving the first string, accepting the invitation to participate in the telecommunications session.

8. A method comprising:
   receiving, at a telecommunications terminal, an invitation to participate in a telecommunications session, wherein conduct of the telecommunications session requires use of a first software application;
   obtaining, at the telecommunications terminal, a first characteristic of use of a component of a second software application, wherein the second software application is executing on the telecommunications terminal;
   transmitting, from the telecommunications terminal, a rejection of the invitation based on the first characteristic of use of the component of the second software application;
   obtaining, at the telecommunications terminal, a second characteristic of use of the component of the second software application; and
   initiating a telecommunications session from the telecommunications terminal when the second characteristic of use of the component of the second software application matches a criterion.

9. The method of claim 8, further comprising receiving, at the telecommunications terminal, an indication of an availability policy, and wherein the rejection of the invitation is also based on the availability policy.

10. The method of claim 8, wherein the first characteristic comprises a Uniform Resource Identifier (URI) to which the second software application established a connection.

11. The method of claim 8, wherein the first characteristic comprises a presence of a keyword.

12. The method of claim 8, wherein the first characteristic comprises an access permission for a document that is open for editing by the second software application.

13. The method of claim 8, wherein the rejection is also based on a characteristic of the invitation to participate in the telecommunications session.

14. The method of claim 8, further comprising:
   receiving a first string at the telecommunications terminal; and
   in response to receiving the first string, accepting the incoming invitation to participate in the telecommunications session.

* * * * *